United States Patent [19]

Peterson et al.

[11] Patent Number: 5,032,116
[45] Date of Patent: Jul. 16, 1991

[54] FLASHBACK PLUG

[75] Inventors: Gerald H. Peterson, Salt Lake City, Utah; Norman B. Winland, Plano, Tex.

[73] Assignee: Becton, Dickinson and Company, Franklin Lakes, N.J.

[21] Appl. No.: 638,957

[22] Filed: Jan. 9, 1991

[51] Int. Cl.$^5$ ............................................. A61M 5/178
[52] U.S. Cl. ..................................... 604/168; 604/900
[58] Field of Search ............... 604/168, 169, 166, 900, 604/164, 126

[56] References Cited

U.S. PATENT DOCUMENTS

| | | | |
|---|---|---|---|
| 4,200,096 | 4/1980 | Charvin | 604/168 X |
| 4,207,870 | 6/1980 | Eldridge | 604/168 X |
| 4,682,980 | 7/1987 | Suzuki | 604/168 X |
| 4,828,587 | 5/1989 | Baurmeister et al. | 604/126 X |
| 4,917,671 | 4/1990 | Chang | 604/168 |

Primary Examiner—John J. Wilson
Assistant Examiner—Jeffrey A. Smith
Attorney, Agent, or Firm—Aaron Passman

[57] ABSTRACT

A flashback plug has a body molded of a semi-transparent polymeric material along and about an axis. A distal end of the body engages in fluid tight communication a needle hub flash chamber and a proximal end extends therefrom to receive a fitting. A passage extends through the body along the axis from the proximal end to the distal end to permit flow therethrough. A vent membrane of a hydrophobic filter media is mounted by its periphery across the passage. The vent membrane is insert molded within the body to capture the proximally extending periphery thereof so that liquid in the passage distal end can not reach the proximal end. The proximal end of the passage has the shape of a female luer taper which terminates distally at the vent membrane. A pair of opposed channels extend longitudinally and parallel to the axis from the vent membranes to the proximal end. The distal end of the body has an outside a male luer for engaging the needle hub flash chamber.

11 Claims, 2 Drawing Sheets

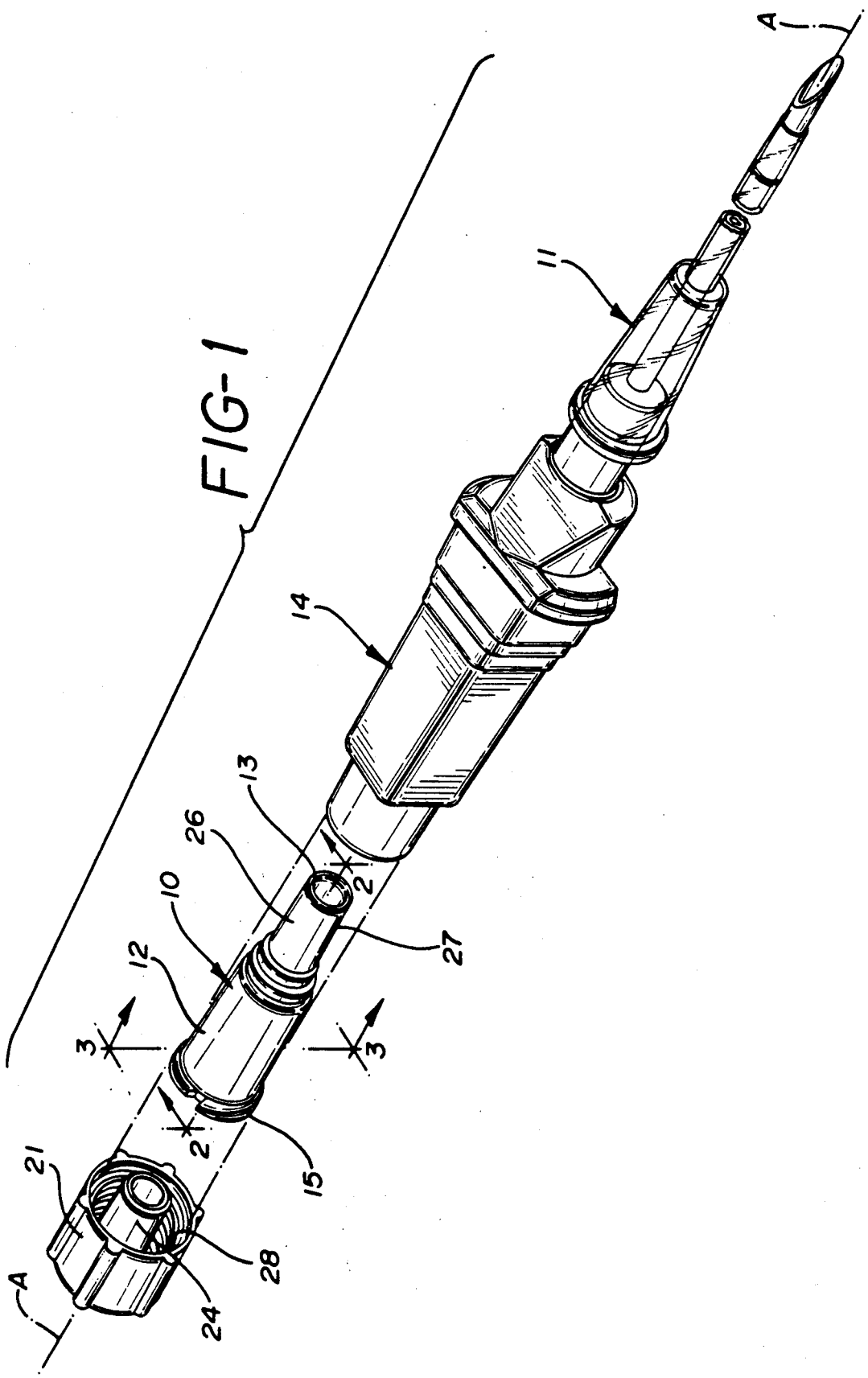

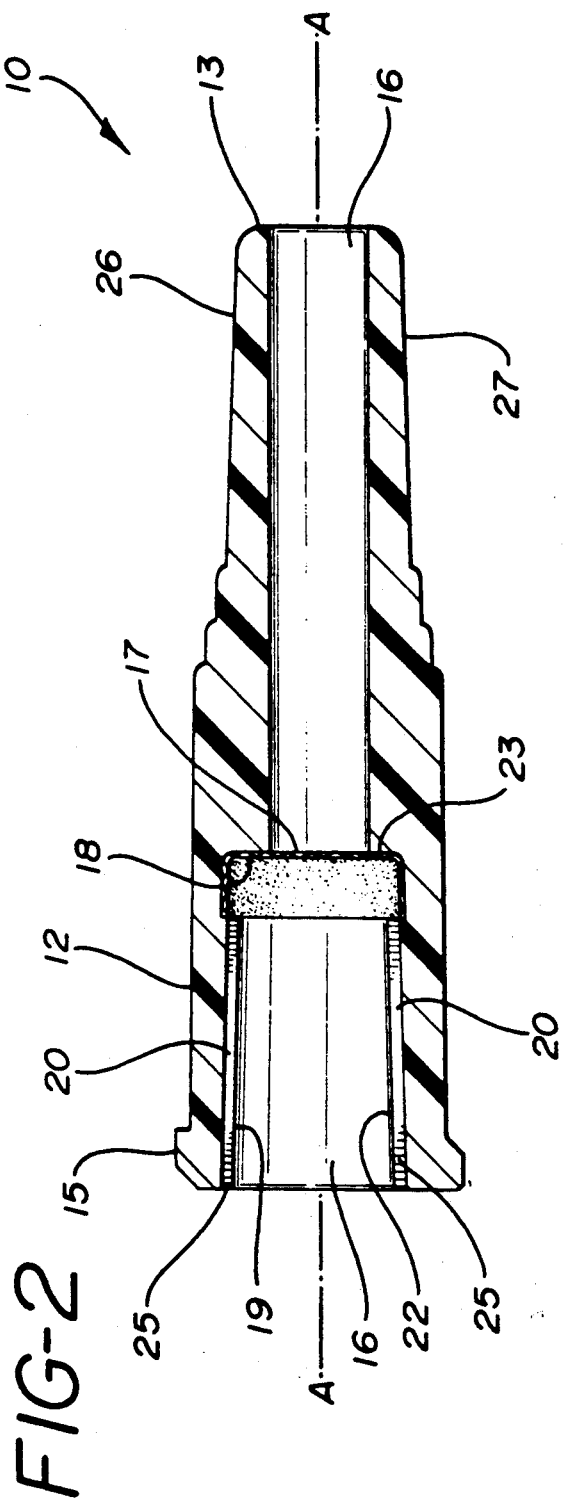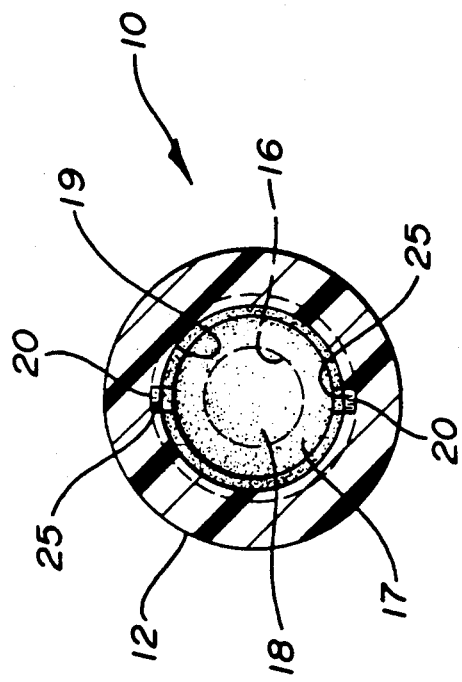

FLASHBACK PLUG

1. Field of the Invention. This invention relates to a bloodless flashback plug for an intravenous over the needle catheter needle hub. The plug includes an integral porous filter material to allow air passage through the plug but not passage of blood and, more particularly, to groove means for venting air from the proximal end of a passage through the flash back plug upon placement of a fitting therewithin.

2. Background. Over the needle catheters are used for peripheral intravenous entry into the vasculature of a patient. The disposable medical product is packaged as an assembly of a catheter adapter with its catheter and a needle and hub assembly conjugated with the catheter adapter such that the needle passes through the catheter tube and extends a slight distance beyond the distal tip thereof to provide a sharpened point for penetration through the skin of the human or animal being catheterized. During catheterization blood flows due to the vascular blood pressure through the hollow needle and into the transparent flash chamber portion of the needle hub so it is visually apparent that the tip of the needle has reached into the blood vessel.

Specifically, after the catheter has been inserted by an over the needle procedure and blood flashback has been observed, the catheter is advanced and/or the needle is withdrawn. After the catheter is inserted into the vessel as desired and the needle is withdrawn and discarded, protection of the medic from patient's blood is desired. Typically the flash chamber is provided with a vent at the proximal end to permit air to leave the flash chamber and allow the chamber to quickly fill with blood when the needle and catheter are properly positioned within the blood vessel. With concern about infection, transmission of AIDS, hepatitis and similar incurable diseases of the blood, methods and devices to prevent blood spillage have become very important and in great demand. Many approaches to flash chambers and early observation have been proposed. Some of them are cumbersome, expensive and interfere with the normal and accepted procedure for the insertion of an over the needle catheter. Typically such chambers vent to the exterior of the needle hub.

After the needle and hub as an assembly are removed from the catheter, the practitioner places a finger against the skin of the human or animal to compress the skin and the vessel therebeneath and distal thereto to for preventing the flow of blood through the catheter tube, into the catheter adapter and out onto the patient and the bedding. The approach disclosed herein does not interfere with or require any additional steps, procedures or cumbersome mechanisms which retard flashback.

U.S. Pat. No. 3,859,998 has a flash chamber plug with a slitted diaphragm to permit the flow of air out of the flash chamber. Because of the viscosity of blood and surface friction, the flow of blood is resisted. U.S. Pat. No. 4,193,400 has a flash chamber plug including three slits to permit air to vent and to restrain the flow of blood. U.S. Pat. No. 4,365,998 has flash chamber with a circuitous maze to inhibit blood flow and permit air venting. U.S. Pat. No. 4,193,399 has a flash plug made of a porous polymeric material which passes air but because of small pore sizes the flow of blood is opposed. The material used therein is ultra high molecular polyethylene made by a scintering process. Such a plug is designed to be pressed into the end of the flash chamber and is held is merely by friction. By nature scintered materials have relatively low elasticity and as such the plug often does not hold tightly within the flash chamber and can actually fall out of position. U.S. Pat. No. 4,046,144 has a proximal placed membrane in a cap for the needle hub to permit air but not blood to escape. U.S. Pat. No. 4,917,671 has the porous insert pushed into place inside the flow control plug from the proximal end and is not captured in both directions except by friction. An improved bloodless flash hub that is easy to connect to is needed.

SUMMARY OF THE INVENTION

The preferred embodiment of a flashback plug for an IV catheter includes a flashback plug body formed along and about an axis. The body is preferably molded of a polymeric material and has a distal end for engaging in fluid tight communication a needle hub flash chamber and has a proximal end for extending therefrom and being open to receive a fitting. A passage extends through the flashback plug body along the axis from the proximal end to the distal end permitting flow therethrough.

A vent membrane of a hydrophobic filter media has a periphery extending proximally and a center sealed across the passage between the distal and proximal ends. The periphery of the vent membrane is insert molded in the flashback body so that liquid in the passage distal end can not reach the passage proximal end. The periphery of the vent membrane acts as an infection barrier by preventing the passage of possibly contaminated blood or other bodily fluids, therethrough.

Groove means longitudinally formed within the inside wall of the passage extend from the vent membrane to the proximal end permitting passage of fluid therewithin to escape even when a fitting has been placed in the passage. The passage at the proximal end of the flashback plug body has in the preferred embodiment a female luer taper. The female luer taper terminates distally with a land against which the vent membrane is located.

The groove means are preferably a pair of opposed channels extending longitudinally and parallel to the axis from the vent membrane to the proximal end. If easily manufactured, any cross sectional shape for the channels, such as semicircular, triangular or free form would be acceptable. The passage extending from the proximal end to the vent membrane is most preferably the mentioned female luer taper having the channels with a square cross section.

The distal end of the flashback body may have an outside shaped with a male luer for engaging the needle hub flash chamber. The passage in the proximal end preferably accepts a male luer fitting of a medical device such as a luer cap stored for later use, or a distal end of a needle cover placed there as a handle to be used during the venipuncture procedure. The vent membrane is preferably placed approximately in the middle of the passageway equidistant between the distal and proximal ends when the flashback plug body is molded thereabout. The polymeric material is preferably semitranslucent to permit observation of blood flash. The vent membrane allows air passage but not the passage of blood from the placed needle to pass through the passage to the proximal end of the plug. The male luer taper of the fitting although seated in the female luer taper of the proximal end of the plug allows air passing through the vent membrane to escape through the channels.

BRIEF DESCRIPTION OF THE DRAWINGS

FIG. 1 is an exploded perspective view of a flashback plug shown as it would fit to a needle hub with a catheter adapter mounted over the needle and a medical device fitting at the proximal end.

FIG. 2 is a cross sectional view of the flashback plug of FIG. 1 taken along lines 2—2 and showing the insert molded vent membrane.

FIG. 3 is a transverse cross sectional view taken along lines 3—3 of FIG. 1 and showing the grooves on opposite sides of the passage through the proximal end.

DETAILED DESCRIPTION OF THE DRAWINGS

While this invention is satisfied by embodiments in many different forms, there is shown in the drawings and will herein be described in detail, a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

FIG. 1 is an exploded perspective view of the preferred embodiment of a flashback plug 10 for an IV catheter 11 comprising a flashback plug body 12 formed along and about an axis A. The body 12 is preferably molded of a polymeric material and has a distal end 13 for engaging in fluid tight communication a needle hub flash chamber 14. The plug 10 has a proximal end 15 for extending from the needle hub flash chamber 14. As shown in the cross section view of FIG. 2, passage 16 extends through the flashback plug body 12 along the axis A from the distal end 13 to the proximal end 15.

As also shown in FIG. 2, a vent membrane 17 of a hydrophobic filter media has a proximally extending periphery 18 molded into the body 12. The vent membrane 17 is across the passage 16 between the distal and proximal ends 13 and 15. The preferred filter media is made by Gelman Sciences, Ann Arbor, Michigan and is a Versapore 800TH Hydrophobic 0.8 um porosity filter membrane. The vent membrane 17 is insert molded into the flashback plug body 12 to capture the proximally extending periphery 18 thereof in an inside wall 19 of the flashback plug body 12 about the passage 16 so that liquid in the passage 16 near the distal end 13 can not reach the proximal end 15.

Groove means 20 are longitudinally formed within the inside wall 19 of the passage 16. The groove means 20 extend from the vent membrane 17 to the proximal end 15 permitting flow therethrough and specifically the escape of gases therein during and after placement of a fitting 21 in the passage 16. The proximal end 15 of the flashback plug body 12 is shaped with a female luer taper 22 terminating distally with a land 23 and positioned for mating with the fitting 21. Fitting 21 has a male luer taper 24 shaped to seat within the female luer taper 22 as shown in FIGS. 1, 2 and 3. The groove means 20 allow the connection of the fitting 21 without concern that gases will be trapped and compressed inside the flashback plug body 12 within the passage 16 near the vent membrane 17 when the fitting 21 is placed thereover.

The groove means 20 is preferably a pair of opposed channels 25 extending longitudinally and parallel to the axis A from the land 23 to the proximal end 15 as shown illustrated in FIG. 2. If easily manufactured, any cross sectional shape for the channels 25, such as semicircular, triangular or free form is exceptable. The passage 16 extending from the proximal end 15 to the vent membrane 17 has the female luer taper 22. Channels 25 that are square in cross section are shown in FIG. 3. The fitting 21 with male luer taper 24 fills much of the female luer taper 22 except for channels 25.

The distal end 13 of the flashback body 12 has an outside shaped nose 26 with a luer taper 27 for engaging in the needle hub flash chamber 14. The passage 16 in the proximal end 15 accepts the male luer taper 24 fitting 21 but any medical device (not shown) with the male luer taper 24 can be fit. Shown for illustrative purposes is fitting 21 as a luer cap with locking threads 28 on the cap to fit over the proximal portion of the flashback plug body 12.

The vent membrane 17 is placed approximately in the middle and transversely across the passage 16 equi-distant between the distal and proximal ends 13 and 15 when the flashback plug body 12 is molded thereabout as shown in the preferred embodiment of FIG. 2. The polymeric material used for the flashback body 12 is preferably semi-translucent polymer to permit observation of blood flash. The vent membrane 17 allows air passage but not the passage of blood from the distal end 13 through the passage 16 to the proximal end 15. The male luer taper 24 of the fitting 21 although seated in the female luer taper 22 of the proximal end 15 allows air passing through the vent membrane 17 to escape through the channels 25.

What is claimed is:

1. A flashback plug for an intravenous over the needle catheter needle hub comprising:
    a flashback plug body formed along and about an axis of a polymeric material, the flashback plug body having a distal end for engaging in fluid tight communicating a needle hub flash chamber and a proximal end for extending from the needle hub flash chamber;
    a passage extending through the flashback plug body along the axis from the proximal end to the distal end of allowing flow therethrough;
    a vent membrane across the passage between the distal and proximal ends and made of a hydrophobic filter media, the vent membrane including a proximally extending periphery insert molded in the flashback plug body and captured thereby so that liquid in the passage near the distal end can not reach the proximal end but gases in the passage may freely communicate between the distal and proximal ends by passing through the vent membrane, and
    groove means ending against the vent membrane and longitudinally formed within an inside wall of the passage, the groove means extending from the vent membrane to the proximal end permitting flow therethrough after placement of a fitting within of the proximal end of the passage, the vent membrane extending across the passage and the distal end of the groove means.

2. The flashback plug of claim 1 wherein the proximal end of the flashback plug body in the passage thereof is shaped as a female luer taper terminating distally with a land.

3. The flashback plug of claim 1 wherein the distal end has an outside male luer thereabout for engaging with a needle hub flash chamber.

4. The flashback plug of claim 1 wherein the groove means are a pair of opposed channels extending longitudinally inside the flashback plug body but exposed to the passage and positioned parallel to the axis from the vent membrane to the proximal end.

5. The flashback plug of claim 4 wherein the passage extending from the proximal end to the vent membrane includes a female luer taper shape and the channels are square in cross section.

6. The flashback plug of claim 5 wherein the distal end has an outside shaped with a male luer for engaging the needle hub flash chamber.

7. The flashback plug body of claim 6 wherein the passage in the proximal end is shaped to accept a male luer fitting.

8. The flashback plug of claim 1 wherein the vent membrane is placed approximately in the middle of the passage substantially equi-distant between the distal and proximal ends when the flashback plug body is molded thereabout.

9. The flashback plug of claim 1 wherein the polymeric material is semitranslucent to permit observation of blood flash.

10. The flashback plug of claim 1 wherein the vent membrane allows air passage but not the passage of blood from the distal end through the passage to the proximal end and the groove means permits the further passage of air from the flashback plug body.

11. A flashback plug for an intravenous over the needle catheter needle hub comprising:
   a feedback plug body formed along and about an axis of a semi-translucent polymer, the flashback plug body having a distal end for engaging in fluid tight communication a needle hub flash chamber and a proximal end for extending from the needle hub flash chamber and wherein the distal end has an outside male luer thereabout;
   a passage extending through the flashback plug body along the axis from the proximal end to the distal end for allowing flow therethrough and wherein the proximal end of the flashback plug body in the passage thereof is shaped as a female luer taper to accept a fitting;
   a vent membrane across the passage between the distal and proximal ends and made of a hydrophobic filter media, the vent membrane including a proximally extending periphery insert molded in the flashback plug body and captured thereby so that liquid in the passage near the distal end can not reach the proximal end but gases in the passage may freely communicate between the distal and proximal ends by passage in through the vent membrane, the vent membrane is placed approximately in the middle of the passage equi-distant between the distal and proximal ends, and
   groove means ending against the vent membrane and longitudinally formed within an inside wall of the passage, the groove means extending from the vent membrane to the proximal end permitting gas flow therethrough after placement of a fitting within the passage from the proximal end and wherein the groove means are a pair of opposed channels extending longitudinally inside the flashback plug body but exposed to the passage and positioned parallel to the axis from the vent membrane to the proximal end and the channels are square in cross section, the vent membrane extending across the passage and the distal end of the groove means.

* * * * *